US012733863B2

(12) United States Patent
Maitre et al.

(10) Patent No.: US 12,733,863 B2
(45) Date of Patent: Sep. 15, 2026

(54) MOVEMENT ASSESSMENT SYSTEM AND METHOD OF USE

(71) Applicant: The Research Institute at Nationwide Children's Hospital, Columbus, OH (US)

(72) Inventors: Nathalie Maitre, Columbus, OH (US); Arnaud Jeanvoine, Columbus, OH (US)

( * ) Notice: Subject to any disclaimer, the term of this patent is extended or adjusted under 35 U.S.C. 154(b) by 329 days.

(21) Appl. No.: 18/289,314

(22) PCT Filed: May 5, 2022

(86) PCT No.: PCT/US2022/027818
§ 371 (c)(1),
(2) Date: Nov. 2, 2023

(87) PCT Pub. No.: WO2022/235897
PCT Pub. Date: Nov. 10, 2022

(65) Prior Publication Data
US 2024/0237937 A1 Jul. 18, 2024

Related U.S. Application Data

(60) Provisional application No. 63/185,043, filed on May 6, 2021.

(51) Int. Cl.
*A61B 5/00* (2006.01)
*A61B 5/11* (2006.01)

(52) U.S. Cl.
CPC .......... *A61B 5/4082* (2013.01); *A61B 5/1126* (2013.01); *A61B 5/7275* (2013.01);
(Continued)

(58) Field of Classification Search
CPC ... A61B 5/4082; A61B 5/1126; A61B 5/7275; A61B 5/742; A61B 2503/045;
(Continued)

(56) References Cited

U.S. PATENT DOCUMENTS

| | | | | |
|---|---|---|---|---|
| 2012/0053491 A1* | 3/2012 | Nathan | ................ | A61B 5/0022 600/595 |
| 2013/0028489 A1* | 1/2013 | Tracton | .................. | G06V 40/20 382/128 |

(Continued)

FOREIGN PATENT DOCUMENTS

CN 110 414 306 A 11/2019

OTHER PUBLICATIONS

European Search Report dated Nov. 4, 2024 in corresponding European patent application No. 22799573.5. (13 pages).

(Continued)

*Primary Examiner* — May A Abouelela
(74) *Attorney, Agent, or Firm* — Watts Law, LLC; Samantha R. Smart

(57) ABSTRACT

A movement assessment system and method of use are described herein. The movement assessment system includes a movement assessment device comprising a plurality of sensors, a movement assessment presentation device having a screen to display image; and a processing device in communication with the movement assessment device and the movement assessment presentation device. The processing device receives displacement data from the movement assessment device. Responsive to receiving the displacement data, the processing device identifies features from displacement data including at least one of motion, amplitude and speed variation of sensed motion, extracts a spectrum from the features to identify feature variability over time, identifies from spectrum potential disease based upon a percentage of abnormal movement over a likelihood threshold being identified, and presents the potential disease to user on the movement assessment presentation device.

20 Claims, 13 Drawing Sheets

(52) U.S. Cl.
CPC ........ *A61B 5/742* (2013.01); *A61B 2503/045* (2013.01); *A61B 2562/0247* (2013.01); *A61B 2562/046* (2013.01)

(58) Field of Classification Search
CPC ...... A61B 2562/0247; A61B 2562/046; A61B 2503/04; A61B 5/1121; A61B 5/6892; A61B 5/7264
See application file for complete search history.

(56) References Cited

U.S. PATENT DOCUMENTS

| | | | | |
|---|---|---|---|---|
| 2013/0310700 | A1* | 11/2013 | Wiard | A61B 5/318 600/500 |
| 2014/0024971 | A1* | 1/2014 | Bunn | A61B 5/1124 600/595 |
| 2014/0153794 | A1* | 6/2014 | Varaklis | G06T 7/0012 382/128 |
| 2016/0198998 | A1* | 7/2016 | Rahimi | A61B 5/4519 600/595 |
| 2017/0188895 | A1* | 7/2017 | Nathan | A61B 5/1118 |
| 2017/0287146 | A1* | 10/2017 | Pathak | G16H 15/00 |
| 2019/0110683 | A1* | 4/2019 | Kim | H04M 1/72418 |
| 2020/0015713 | A1* | 1/2020 | Chang | G01P 15/00 |
| 2020/0129109 | A1* | 4/2020 | Bunn | A61B 5/7264 |
| 2020/0367810 | A1* | 11/2020 | Shouldice | A61B 5/4818 |
| 2020/0375500 | A1* | 12/2020 | Soriano | A61B 5/002 |
| 2020/0383635 | A1* | 12/2020 | Soe | A61B 5/7275 |
| 2021/0073522 | A1* | 3/2021 | Sugawara | A61B 5/1128 |
| 2021/0128024 | A1* | 5/2021 | Battista | A61B 5/4082 |
| 2021/0197833 | A1* | 7/2021 | Yoshida | A61B 5/1128 |
| 2021/0315486 | A1* | 10/2021 | Delp | G16H 50/50 |
| 2021/0321877 | A1* | 10/2021 | Fields | A61B 6/466 |
| 2022/0007965 | A1* | 1/2022 | Tiron | A61B 5/0823 |
| 2022/0022750 | A1* | 1/2022 | Fotiadis | G16H 40/67 |
| 2022/0079514 | A1* | 3/2022 | Main | A61B 5/4812 |
| 2022/0117514 | A1* | 4/2022 | Kuhn | A61B 5/743 |
| 2022/0157143 | A1* | 5/2022 | Panneer Selvam | G04G 9/007 |
| 2022/0176545 | A1* | 6/2022 | Robison | A61B 5/1038 |
| 2022/0225943 | A1* | 7/2022 | Komine | A61B 5/11 |
| 2022/0248980 | A1* | 8/2022 | Devani | G06N 3/09 |
| 2022/0257146 | A1* | 8/2022 | Anderson | G01S 13/08 |
| 2022/0280098 | A1* | 9/2022 | Hao | A61B 5/0004 |
| 2022/0313098 | A1* | 10/2022 | LeBoeuf | A61B 5/7221 |
| 2023/0157552 | A1* | 5/2023 | Thuering | A61B 5/4848 600/301 |
| 2023/0270354 | A1* | 8/2023 | Huang | A61B 5/112 |

OTHER PUBLICATIONS

Stahl, A. et al. An Optical Flow Based Method to Predict Infantile Cerebral Palsy. IEEE Transactions on Neural Systems and Rehabilitation Engineering, IEEE, USA, Jul. 1, 2012, pp. 605-614; vol. 20, No. 4. (10 pages).

Marschik, Peter B. et al. A Novel Way to Measure and Predict Development: A Heuristic Approach to Facilitate the Early Detection of Neurodevelopmental Disorder. Current Neurology and Neuroscience Reports, Springer US, New York, Apr. 8, 2017, pp. 1-15; vol. 17, No. 5. (15 pages).

Rihar, Andraz et al. Using sensory data fusion methods for infant body posture assessment. 2015 IEEE/RSJ International Conference on Intelligent Robots and Systems (IROS), IEEE, Sep. 28, 2015, pp. 292-297. (6 pages).

Anonymous Nelson et al. The future of General Movement Assessment: The role of computer vision and machine learning—A scoping review—ScienceDirect. Research in Developmental Disabilities, Mar. 1, 2021, vol. 110, p. 103854. (1 page).

Rihar, Andraz et al. Sensory data fusion of pressure mattress and wireless inertial magnetic measurement units. Medical and Biological Engineering and Computing, Springer, Heildelberg, DE, Nov. 4, 2014, vol. 53, No. 2, pp. 123-135. (13 pages).

European Examination Report in corresponding European application No. 22 799 573.5, dated Mar. 3, 2026. (8 pages).

* cited by examiner

304

310

Spectrum

312D

312B

312C

312A

312E 22
20
18
16
14
12
10
8
6
4
2

2 4 6 8 10 12 14

Frequency (Hz)

1300

1400

MOVEMENT ASSESSMENT SYSTEM AND METHOD OF USE

CROSS REFERENCE TO RELATED APPLICATIONS

The following is a U.S. national phase patent application filed under 35 U.S.C. § 371 claiming priority to international patent application serial number PCT/US22/027818 having a filing date of May 5, 2022 and having been published by the International Bureau as publication number WO 2022/235897 on Nov. 10, 2022, which claims priority under 35 U.S.C. § 119 (e) to U.S. Provisional Patent Application Ser. No. 63/185,043 filed May 6, 2021 entitled MOVEMENT ASSESSMENT SYSTEM AND METHOD OF USE. The entire contents of the above-identified applications, and publication from which priority is claimed, are incorporated herein by reference in their entireties for all purposes.

TECHNICAL FIELD

The present disclosure generally relates to an assessment system and method of use, and more particularly to an assessment system for general movement assessment to identify and/or predict neuromotor disorders.

BACKGROUND

Early detection of neuromotor disorders in the neonatal intensive care unit (NICU) can allow targeted evaluation of infants and parent support. Prechtl's General Movements Assessment (GMA) allows visual recognition of movement patterns that, when cramped synchronized (CS) have high specificity in predicting neuromotor disorders. However, challenges inherent to various healthcare settings and to the rigorous GMA training process, have hindered universal adoption for use with newborns.

Infants in a NICU environment are more likely to develop neuro-motor disorders associated with other conditions, such as prematurity, birth depression, congenital heart defects, genetic or congenital syndromes. The burden of disability for these children and their families is far greater than motor consequences. Throughout their lifetime, the babies having developed the neuro-motor disorders will suffer and have delays or impairments in cognitive, communication, sensory and social-emotional domains as well as preventable co-morbidities in vision, hearing, feeding, pain, sleep and uncontrolled epilepsy.

Early and targeted surveillance and medical, surgical or developmental interventions is critical to changing their outcomes. Yet early surveillance is highly variable due to inconsistencies in practice, limited resources in many settings and difficulties in access to care after children leave the hospital. The time preceding discharge from the NICU is ideal for screening of infants at high-risk for neuro-motor disorders such as Cerebral Palsy (CP), because infants are easily accessible for bedside assessments and interventions For example, CP, the most common physical disability in the United States (US) and in the world, is poorly assessed. Many individuals with CP suffer from developmental disregard, or the inability of the brain to "see" an affected hand (e.g., neglect), which then leads to poor sensory and motor function in the affected hand. Similarly, neglect of this nature often affects the approximately 800,000 adults in the US who suffer from stroke.

Currently, there are no clinical assessments that precisely quantify developmental disregard and/or neglect of an extremity. Known research assessments typically do not translate into clinical practice because they are based on subjective evaluations of behavior, and/or are not quantitative. Known research assessments often confuse cognitive ability with visuo-motor and/or tactile performance.

Current research assessments for CP require large, prohibitively expensive, and complex equipment. The lack of clinical assessments makes it problematic to accurately measure progress in a particular individual, which in turn makes it difficult to determine whether therapies are helping (e.g., improving the outcome for) the particular individual. Further, effective therapies for upper extremity use in CP and/or other like physical disabilities often involve rewiring of sensory/motor pathways in the affected hand, but also of bilateral hand movements. The condition (CP) and/or the affected hand have to be identified for effective rehabilitation strategies such as bimanual intensive therapy to be implemented. Currently effective therapies are uncoupled from effective testing.

SUMMARY

One aspect of the present disclosure comprises a movement assessment system that includes a movement assessment device comprising a plurality of sensors, a movement assessment presentation device having a screen to display image; and a processing device in communication with the movement assessment device and the movement assessment presentation device. The processing device receives displacement data from the movement assessment device. Responsive to receiving the displacement data, the processing device identifies features from displacement data including at least one of motion, amplitude and speed variation of sensed motion, extracts a spectrum from the features to identify feature variability over time, identifies from spectrum potential disease based upon a percentage of abnormal movement over a likelihood threshold being identified, and presents the potential disease to user on the movement assessment presentation device.

Another aspect of the present disclosure comprises a non-transitory computer readable medium storing instructions executable by an associated processor to perform a method for implementing a movement assessment system. The method including receiving movement data from a movement assessment device comprising a plurality of sensors, the movement data based upon movement of an human on the movement assessment device as detected by the plurality of sensors, plotting recorded movement based upon the movement data taken over a first duration to generate displacement data, and normalizing the displacement data as first, second, third, fourth, and fifth quintets comprising first, second, third, fourth, and fifth areas comprising one or more sensors of the plurality of sensors, the normalizing the displacement data generating normalized quintet data. The method further comprising generating two clusters per quintet as clustered data from the normalized quintet data, and generating extracted data. The generating the extracted data comprising identifying a first percentage of time the first of the two clusters per quintet is active relative to a second percentage of time the second of the two clusters per quintet is active, calculating a center of mass of each cluster of each quintet based upon the first and second percentages, and calculating a distance between the center of mass of a core quintet and the centers of mass of peripheral quintets. The method further comprising classifying the extracted data to identify a disease probability.

Yet another aspect of the present disclosure comprises a movement assessment system comprising a movement assessment device comprising a plurality of pressure sensors, a movement assessment presentation device having a screen to display images, and a processing device in communication with the movement assessment device and the movement assessment presentation device, the processing device receiving displacement data from the movement assessment device, wherein responsive to receiving the displacement data. The processing device identifies quintets comprising one or more sensors of the plurality of sensor of the movement assessment device, extracts features from each of the quintets to generate a set of five features, generates a set of five spectrums from the set of five features, each of the set of five spectrums reflecting sensed displacement data in one of the quintets, respectively. Further, the processing device identifies from the set of five spectrums percentages of normal movement and abnormal movement, identifies potential disease based upon the percentage of the abnormal movement over a likelihood threshold being identified, and presents the potential disease to user on the movement assessment presentation device.

BRIEF DESCRIPTION OF THE DRAWINGS

The foregoing and other features and advantages of the present disclosure will become apparent to one skilled in the art to which the present disclosure relates upon consideration of the following description of the disclosure with reference to the accompanying drawings, wherein like reference numerals, unless otherwise described refer to like parts throughout the drawings and in which.

Figure 1:
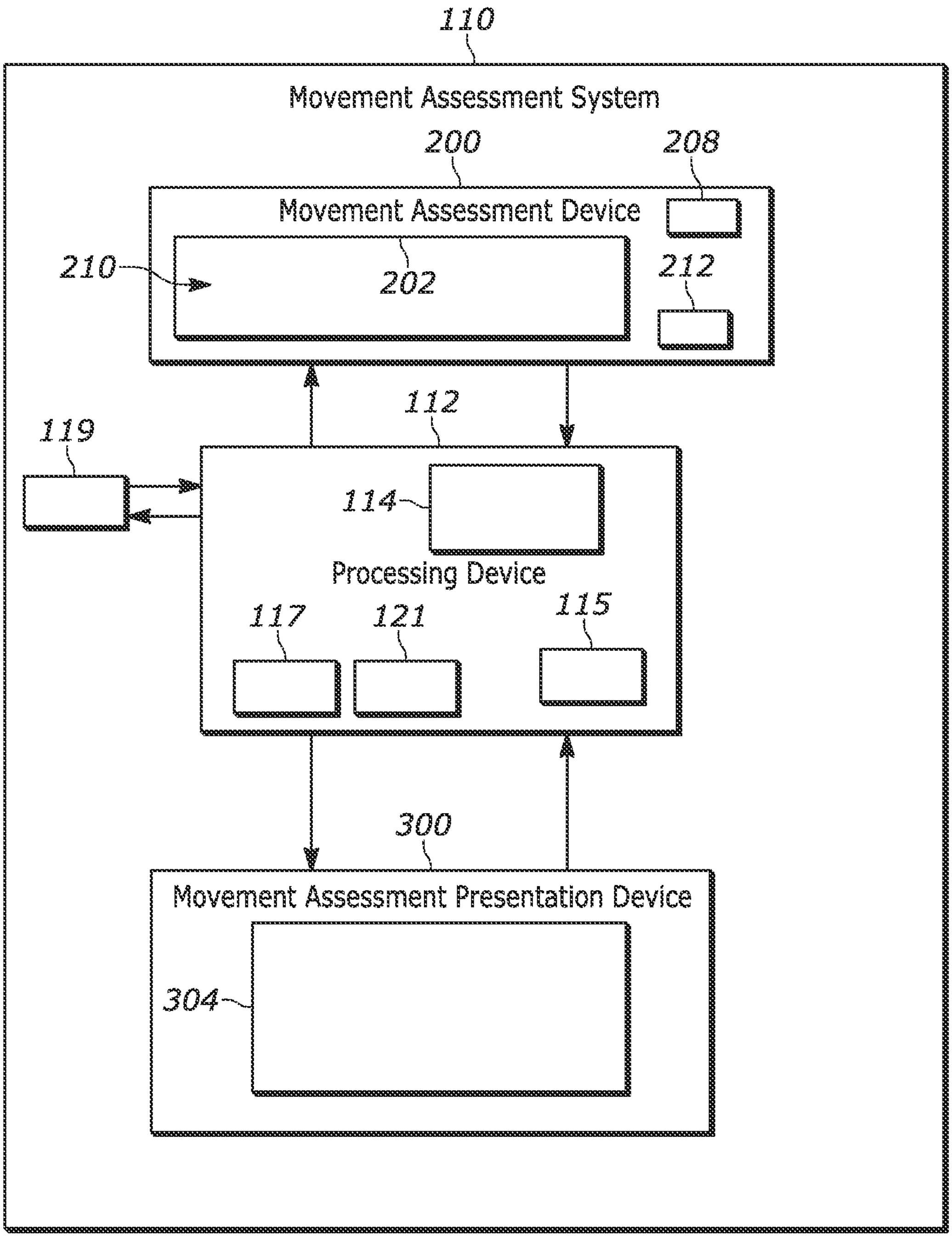
FIG. 1 is a schematic diagram of a movement assessment system for supporting an movement assessment device, in accordance with one example embodiment of the present disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

The apparatus and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

Referring now to the figures generally wherein like numbered features shown therein refer to like elements throughout unless otherwise noted. The present disclosure generally relates to an assessment system and method of use, and more particularly to an assessment system for monitoring and/or measuring neurologic function, neurologic and/or muscular fatigue, and/or variation in cognitive and/or motion variables.

FIG. 1 illustrates a schematic diagram of a movement assessment system 100, in accordance with one of the exemplary embodiments of the disclosure. The movement assessment system 100 includes a processing device 112. In one example embodiment, the processing device 112 includes a computing device 115 (e.g. a database server, a file server, an application server, a computer, or the like) with computing capability and/or a processor 114. The processor 114 comprises central processing units (CPU), such as a programmable general purpose or special purpose microprocessor, and/or other similar device or a combination thereof.

The processing device 112 would generate outputs based upon inputs received from a movement assessment device 200 and/or a movement assessment presentation device 300, cloud storage, a local input form a user, etc. It would be appreciated by one having ordinary skill in the art that in some embodiments the processing device 112 would include a data storage device 117 in various forms of non-transitory, volatile, and non-volatile memories which would store buffered or permanent data as well as compiled programming codes used to execute functions of the processing device 112. In another example embodiment, the data storage device 117 can be external to and accessible by the processing device 112. In yet another example embodiment, the data storage device 117 includes an external hard drive, cloud storage, and/or other external recording devices 119.

In one example embodiment, the processing device 112 comprises one of a remote or local computer system 121. The computer system 121 includes desktop, laptop, tablet hand-held personal computing device, IAN, WAN, WWW, and the like, running on any number of known operating systems and are accessible for communication with remote data storage, such as a cloud, host operating computer, via a world-wide-web or Internet.

In another example embodiment, the processing device 112 comprises a processor, a microprocessor, a data storage, computer system memory that includes random-access-memory ("RAM"), read-only-memory ("ROM") and/or an input/output interface. The processing device 112 executes instructions by non-transitory computer readable medium either internal or external through the processor that communicates to the processor via input interface and/or electrical communications, such as from the movement assessment device 200 and/or the movement assessment presentation device 300. In yet another example embodiment, the processing device 112 communicates with the Internet, a network such as a LAN, WAN, and/or a cloud, input/output devices such as flash drives, remote devices such as a smart phone or tablet, and displays.

In one example embodiment, the movement assessment presentation device 300 includes an interactive display 304, the display for receiving tactile input. In one example embodiment, the movement assessment presentation device 300 includes a secondary device, such as a smart phone, tablet, or the like. In another example embodiment, the processing device 112, an SD-card-writer (e.g., for data retrieval), and the interactive display 304 (e.g., a touch-screen status-and-control LCD display) are housed in a separate module connected to the processing device 112 and/or the movement assessment device 200 via short range wireless signals, WIFI, and/or corded communication.

As illustrated in FIGS. 2A-2D, the movement assessment device 200 comprises a flat or planar surface supporting a plurality of sensors 210 in a sensing area 202. In one embodiment, the movement assessment device 200 supports a grid of 32×32 sensors 210 (see FIG. 2B). On example of the movement assessment device 200 is the BodiTrak mat system made by VistaMedical. The plurality of sensors 210 are pressure sensors, such as, for example, resistive, capacitive, piezoelectric, and/or micro electro-mechanical system (MEMS) sensors. In one example embodiment, the movement assessment device 200 supports the plurality of sensors 210 arranged in an array in which some or all of the sensors 210 are not evenly spaced from each other sensor. In this example embodiment, the orientation of an infant or child relative the sensing area 202 impact the quality of movement comparison between infants and children.

Figure 12:
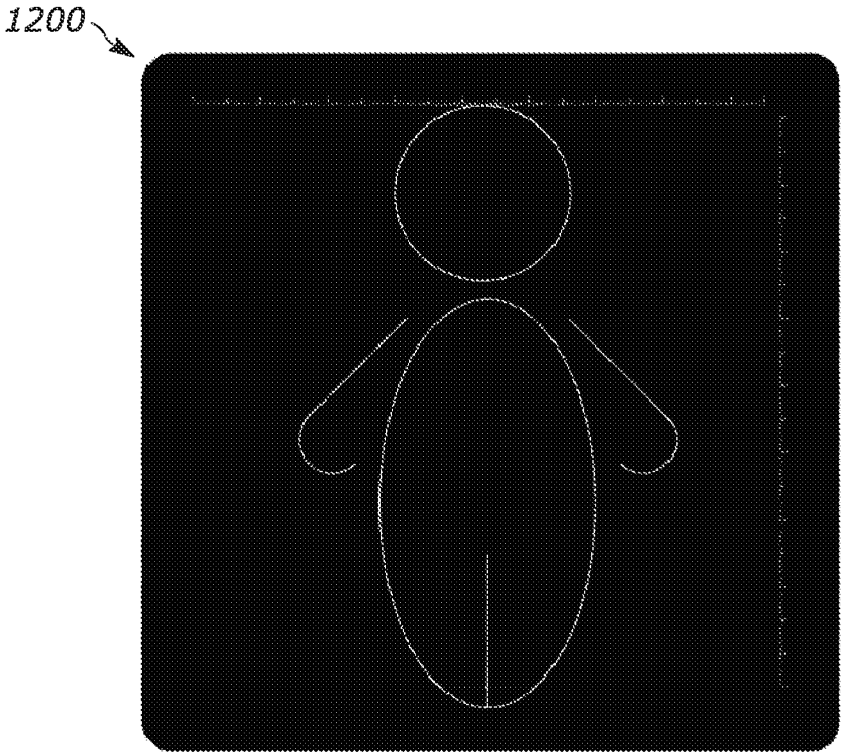
FIG. 12 illustrates a first view of a top surface of a movement assessment device, in accordance with one example embodiment of the present disclosure.
Figure 13:
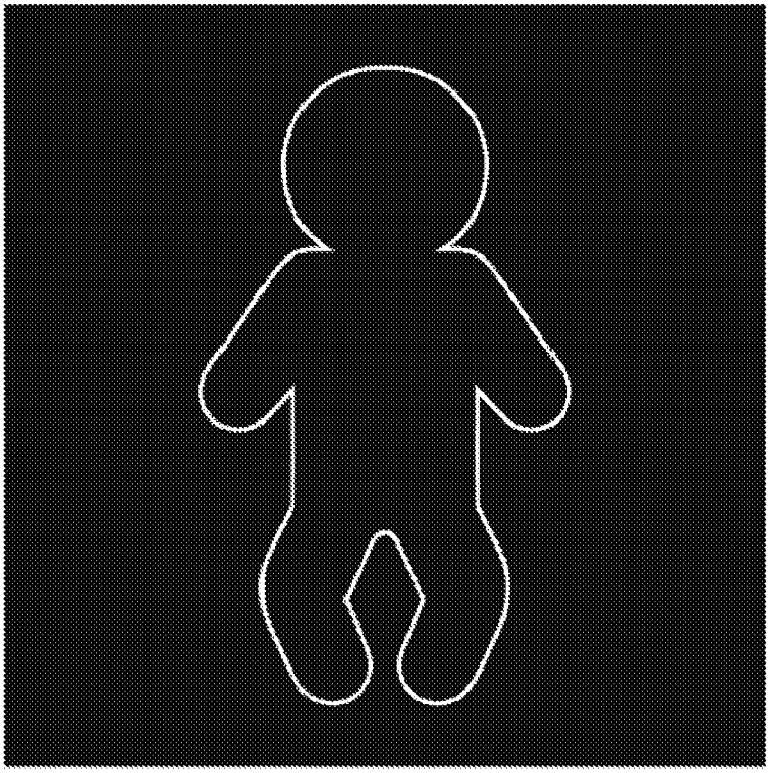
FIG. 13 illustrates a second view of a top surface of a movement assessment device, in accordance with one example embodiment of the present disclosure.
Figure 14:
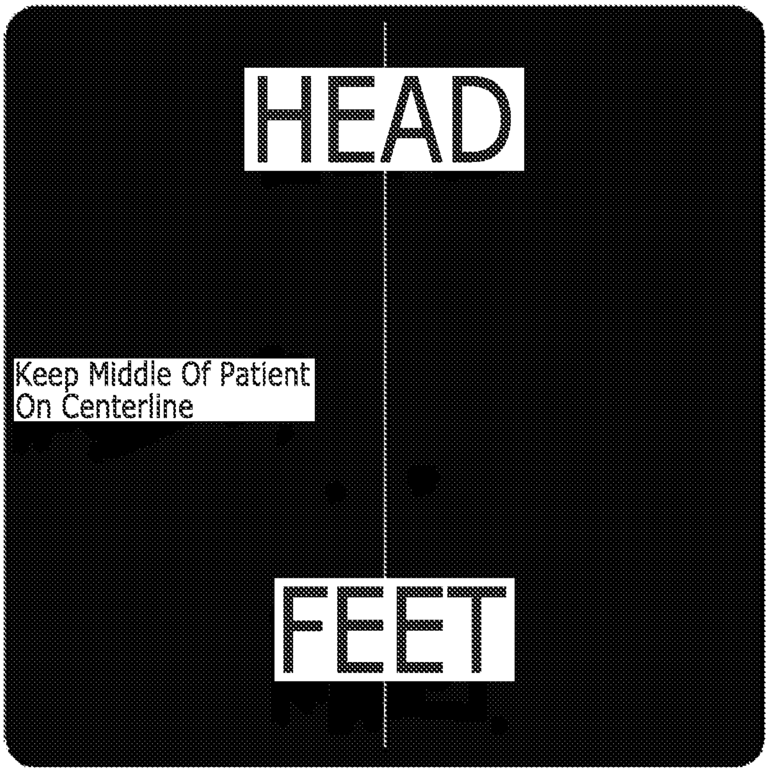
FIG. 14 illustrates a third view of a top surface of a movement assessment device, in accordance with one example embodiment of the present disclosure.

The movement assessment device 200 is covered by a plastic, fabric, such as natural materials (e.g., cotton or linen sheets) or artificial materials (e.g., polyester sheets), or other material that allows for identifying a change in pressure on the plurality of sensors 210. In another example embodiment, the movement assessment device 200 is covered by surface labeling, such as the surface labeling 1200, 1300, 1400 illustrated in FIGS. 12-14. The surface labeling 1200 illustrated in FIG. 12 outlines a head, two arms, a torso, and bottom half of an infant or child. The surface labeling 1300 illustrated in FIG. 13 outlines a head, two arms, a torso, and two legs of an infant or child. The surface labeling 1400 illustrated in FIG. 14 presents text indicating where a head and feet of an infant or child should be placed, as well as text and a line graphic illustrating a centerline along which the infant or child should be placed. The surface labeling 1200, 1300, 1400 maximizes consistency and repeatability of infant or child placement across users, and create a more unform orientation of the infant or child relative the sensing area 202.

As in the illustrated embodiment of FIG. 1, the movement assessment device 200 has a power source 208. In one example embodiment, the power source 208 is one of cordless (e.g., battery) or corded. In another example embodiment, the movement assessment device 200 defines a communication apparatus 212. In one example embodiment, the communication apparatus 212 communicates with the processing device 112 through short wave radio waves (Bluetooth), WIFI, and/or corded communication. The sensing area 202 sends sensed pressure information to the processing device 112, wherein the processing device divides portions of the sensing area into first, second, third, fourth, and fifth quintets **202*a*, 202*b*, 202*c*, 202*d*, and 202*e***.

Figure 5:
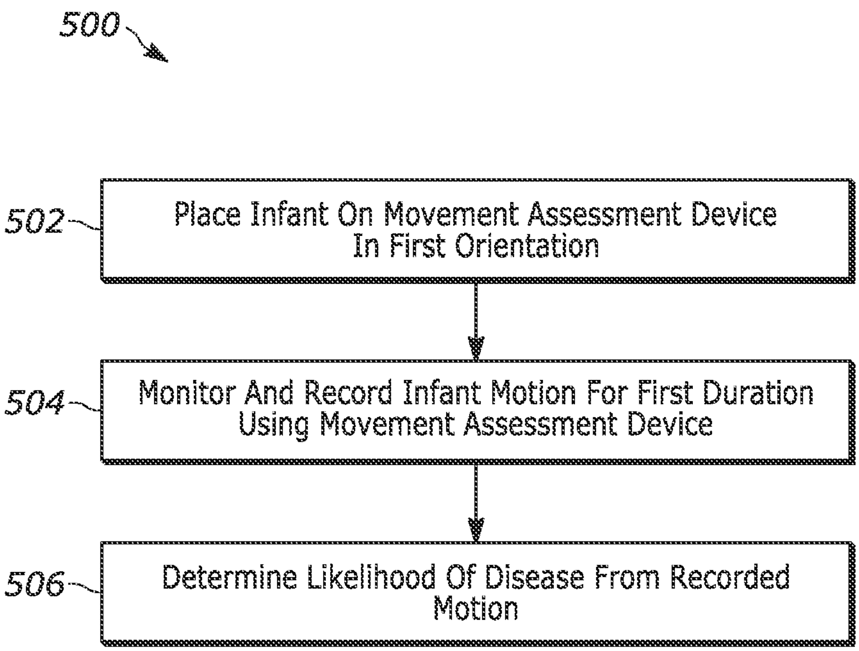
FIG. 5 illustrates a flow diagram for a method of using a movement assessment system in accordance with one example embodiment of the present disclosure.

As shown in the example embodiment of FIG. 5, a method 500 includes steps of using the movement assessment device 200. At 502, an infant or child is placed on the movement assessment device 200 in a first orientation. In one example embodiment, the first orientation places a head of the infant or child at or near the first and second quintets **202*a*, 202*b*, the body of the infant over the third quintet 202*c*, and the lower body of the infant over the fourth and fifth quintets 202*d*, 202*e* consistent with the surface labeling 1200, 1300, 1400 (see, FIGS. 12-14). In one embodiment, the movement assessment device 200 omits the surface labeling 1200, 1300, 1400. It would be appreciated that other orientations relative to first orientation are contemplated, such as a flip (e.g., using an opposite side of the movement assessment device 200), a translation, a primary rotation (e.g., a rotation that is in an increment of 90 degrees), a secondary rotation (e.g., a rotation that is between 0 and 90 degrees), or any combination thereof. Advantageously, the surface labeling 1200, 1300, 1400 provides a consistent visual cue to providers. Use of the surface labeling 1200, 1300, 1400 on a single side of the movement assessment device 200 eliminates flip orientation changes between different infants and children. Use of the surface labeling 1200, 1300, 1400 will eliminate primary rotation changes. Further, use of the surface labeling 1200, 1300, 1400 minimizes translation and secondary rotations by including a centerline target or anthropomorphic graphic centered on the plurality of sensors 210**.

Figure 2A:
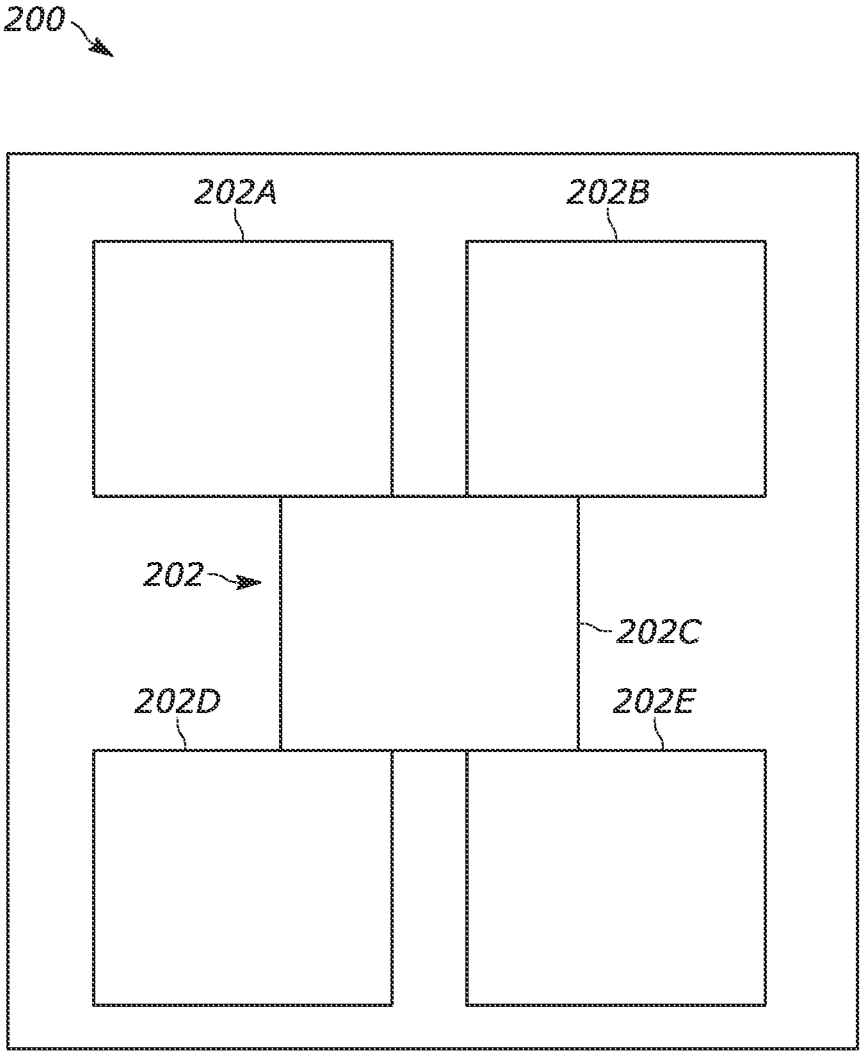
FIG. 2A illustrates a top plan view of a movement assessment device in accordance with one example embodiment of the present disclosure.
Figure 2B:
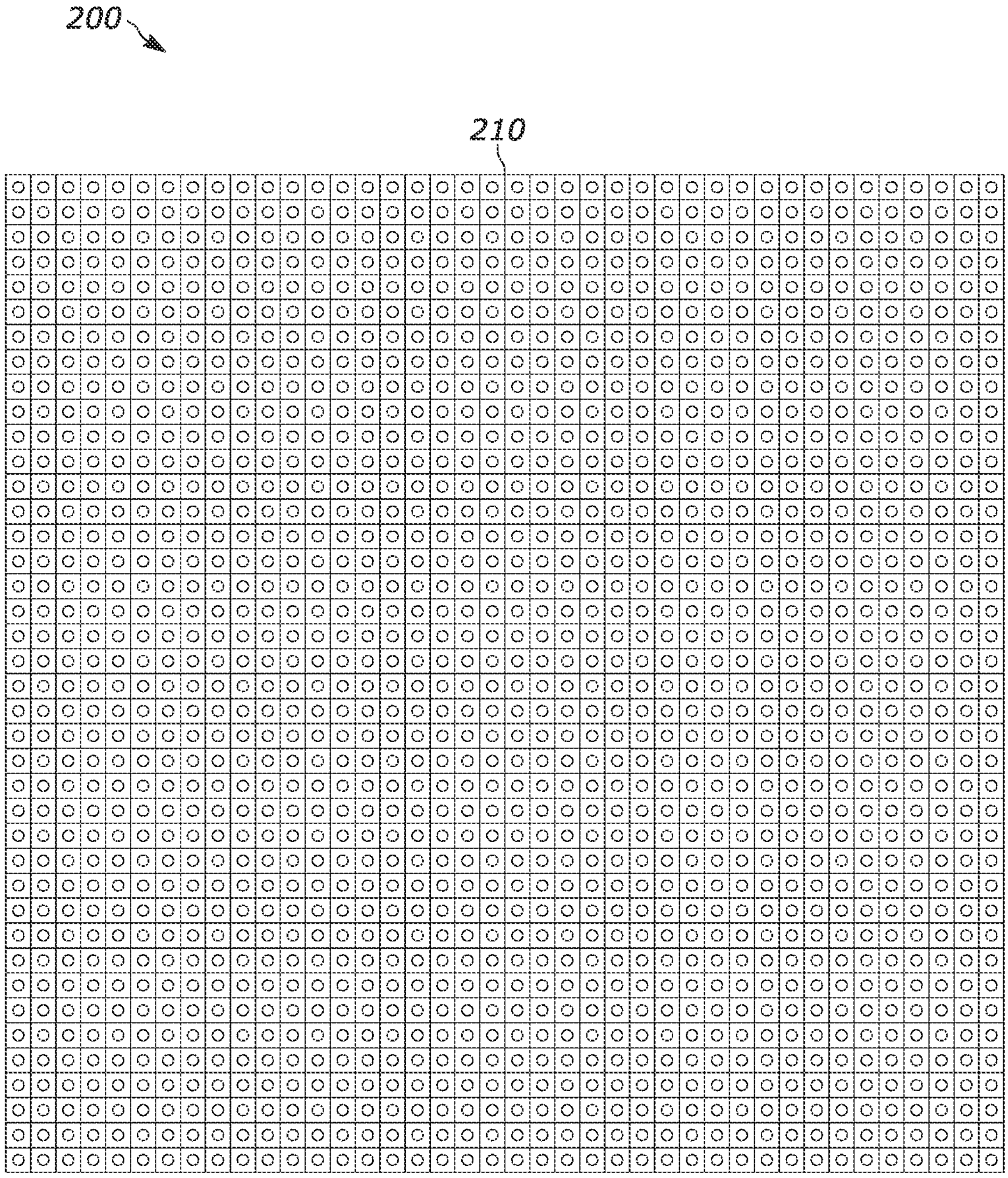
FIG. 2B illustrates a schematic view of sensors of a movement assessment device in accordance with one example embodiment of the present disclosure.
Figure 2C:
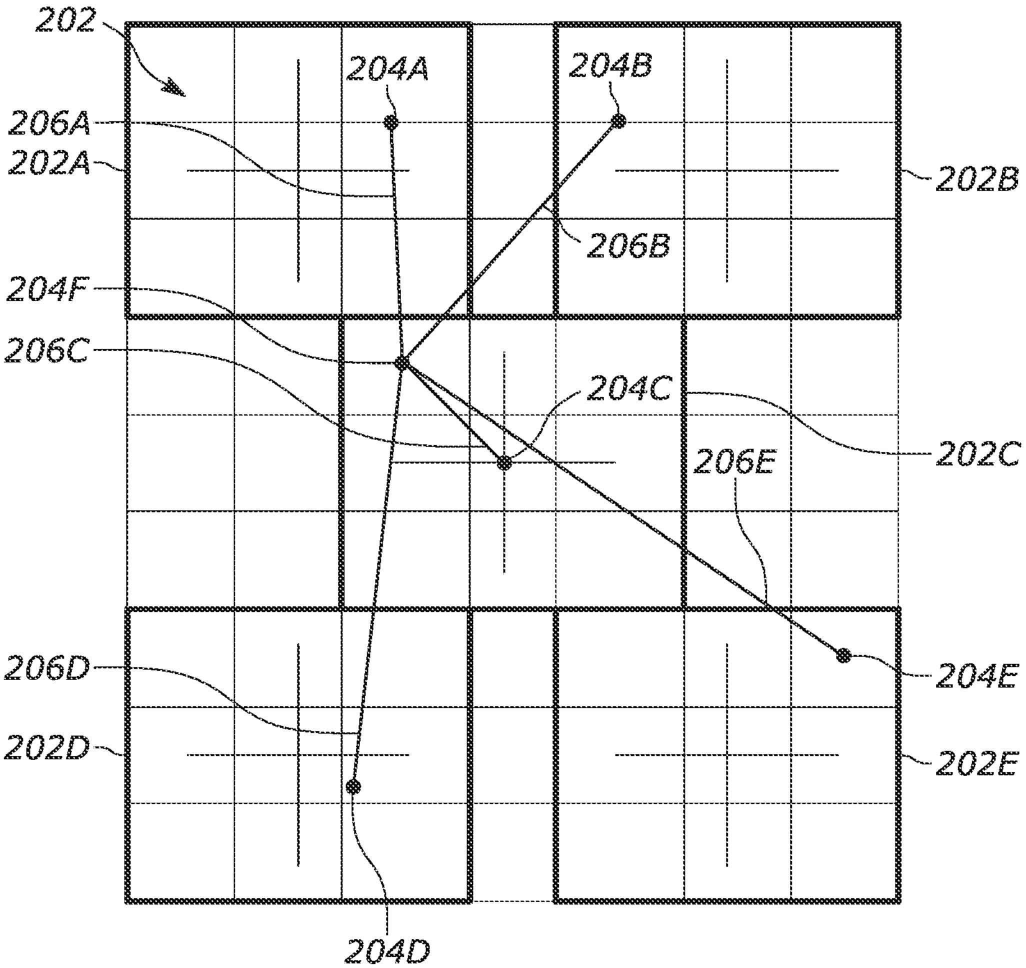
FIG. 2C illustrates a schematic view of a quintet formed by a movement assessment device in accordance with one example embodiment of the present disclosure.
Figure 2D:
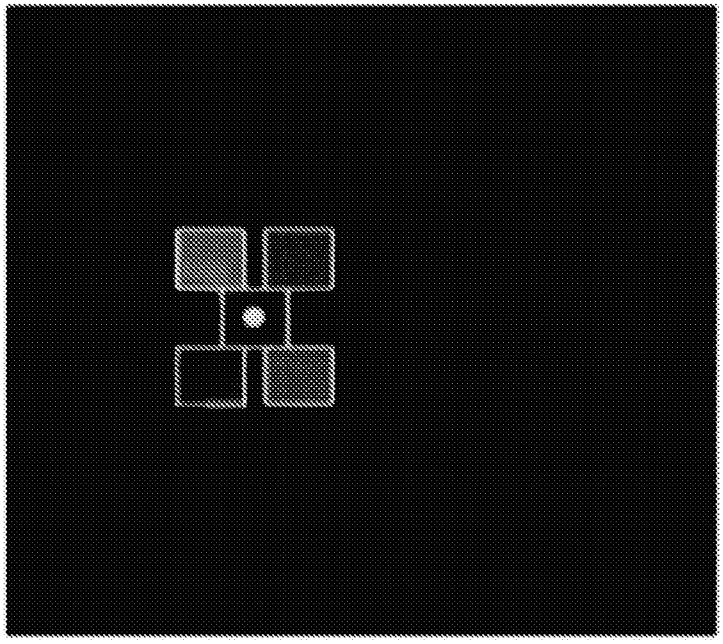
FIG. 2D illustrates a schematic view of a quintet formed by a movement assessment device in accordance with one example embodiment of the present disclosure.

In another example embodiment, the processing device 112 assigns the quintets **202*a*, 202*b*, 202*c*, 202*d*, and 202*e* after the infant has been placed on the sensing area 202, based upon a sensed orientation of the infant, such that the head of the infant is at or near the first and second quintets 202*a*, 202*b*, the body of the infant is over the third quintet 202*c*, and the lower body of the infant is over the fourth and fifth quintets 202*d*, 202*e*. In this example embodiment, the movement assessment device 200 sends sensor data collected by the plurality of sensors 210 to the processing device 112, wherein the processing device divides the plurality of sensors into the quintets 202*a*, 202*b*, 202*c*, 202*d*, and 202*e*, as illustrated in FIGS. 2A, 2C and 2D**

At 504, infant motion is monitored and recoded by the plurality of sensors 210 for a first duration (e.g., 1 min to about 3 mins). In another example embodiment, the first duration is 2 minutes. In one example embodiment, the processing device 112 time stamps the sensor data collected by the plurality of sensors 210 to generate the recorded motion (as collected by the plurality of sensors 210). At 506, the movement assessment system 100 determines the likelihood of disease (e.g., identifies normal v. abnormal motion) from the recorded motion. In one example embodiment, the movement assessment system 100 determines that the recorded motion is over a likelihood threshold (e.g., more likely to show abnormal motion than normal motion) and presents suggested further tests/recommended evaluations that the infant should undergo on the movement assessment presentation device 300.

Figure 6:
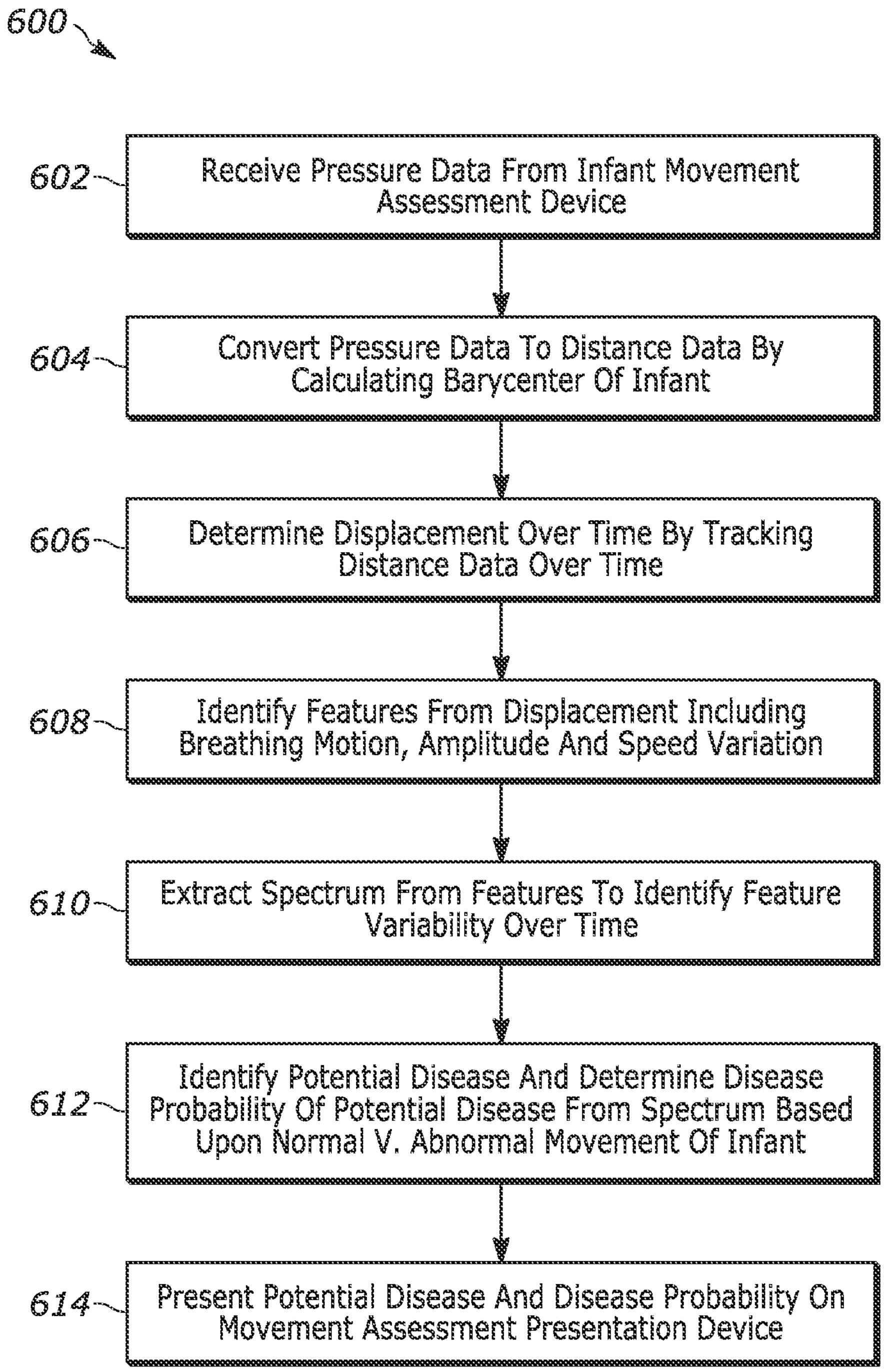
FIG. 6 illustrates a flow diagram for a method of acquiring displacement data and identifying potential diseases using a movement assessment system in accordance with one example embodiment of the present disclosure.

As shown in the example embodiment of FIG. 6, a method 600 includes steps of utilizing the movement assessment system 100. At 602, pressure data is received from the movement assessment device 200. In one example embodiment, the processing device 112 receives the pressure data from the movement assessment device 200. At 604, the pressure data is converted to distance data by calculating the barycenter 204 of the infant (see FIG. 2C). In one example embodiment, such as illustrated in FIG. 2C, the barycenter 204 is calculated for each quintet 202*a*-202*e*, wherein the barycenter is the center of mass of two or more bodies that orbit one another and is the point about which the bodies orbit. In this example embodiment, a third barycenter 204*c* is the center of the third quintet 202*c* (e.g., the point about which the bodies orbit), a first barycenter 204*a* is calculated for the first quintet 202*a*, a second barycenter 204*b* is calculated for the second quintet 202*b*, a fourth barycenter 204*d* is calculated for the fourth quintet 202*d*, and/or a fifth barycenter 204*e* is calculated for the fifth quintet 202*e*. (see FIG. 2C). It would be understood by one having ordinary skill in the art that the barycenter of any of the quintets could be the point about which the bodies orbit.

Figure 3:
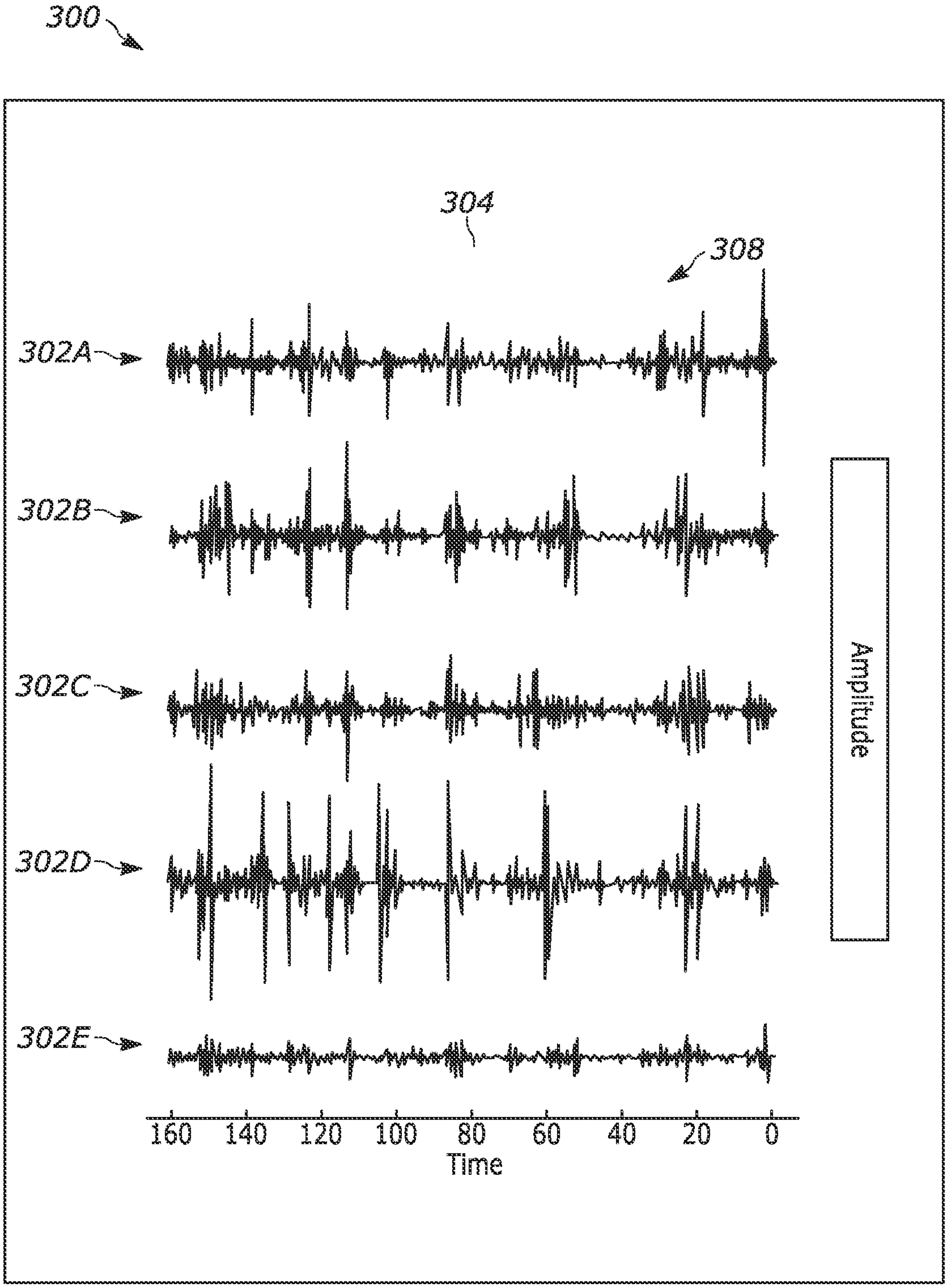
FIG. 3 illustrates a first chart view of an output of a movement assessment device displayed on a movement assessment presentation device, in accordance with one example embodiment of the present disclosure.

At 606, displacement over time of the infant is determined by tracking the distance data over time. In one example embodiment, such as illustrated in FIG. 2A, the displacement is the change in the barycenter's 202*b*-202*e* over time. At 608, features from the displacement data, including breathing motion, amplitude, and/or speed variation are identified. In one example embodiment, the breathing motion is identified in the third quintet 202*c*. In another example embodiment, the amplitude and/or speed variation are identified by quintet 202*a*-202*e*. The amplitude measures the change in pressure, where higher pressure from a given sensor results in a higher amplitude and a lower pressure results in a lower amplitude. In yet another example embodiment, the speed variation is identified by changes in the barycenter's 204*a*-204*b*, 204*d*-204*e* over time in the respective quintets 202*a*-202*b*, 202*d*-202*e*. In one example embodiment, such as illustrated in FIG. 3, amplitudes over time 308 are displayed on the movement assessment display device 300. In one example embodiment the amplitudes over time 308 are extracted for each quintet 202, such that a first amplitude 302*a* represents movement, represented as an amplitude, over time in the first quintet 202*a*, a second amplitude 302*b* represents movement, represented as an amplitude, over time in the second quintet 202*b*, a third amplitude 302*c* represents movement, represented as an amplitude, over time in the third quintet 202*c*, a fourth amplitude 302*d* represents movement, represented as an amplitude, over time in the fourth quintet 202*d*, and a fifth amplitude 302*e* represents movement, represented as an amplitude, over time in the fifth quintet 202*e*. In one example embodiment, the amplitudes over time 308 are displayed on the movement assessment presentation device 300 in real time and/or after the first duration is complete. In another example embodiment, the amplitudes over time 308 are stored and analyzed by the processing device 112 and not presented to the user.

Figure 4:
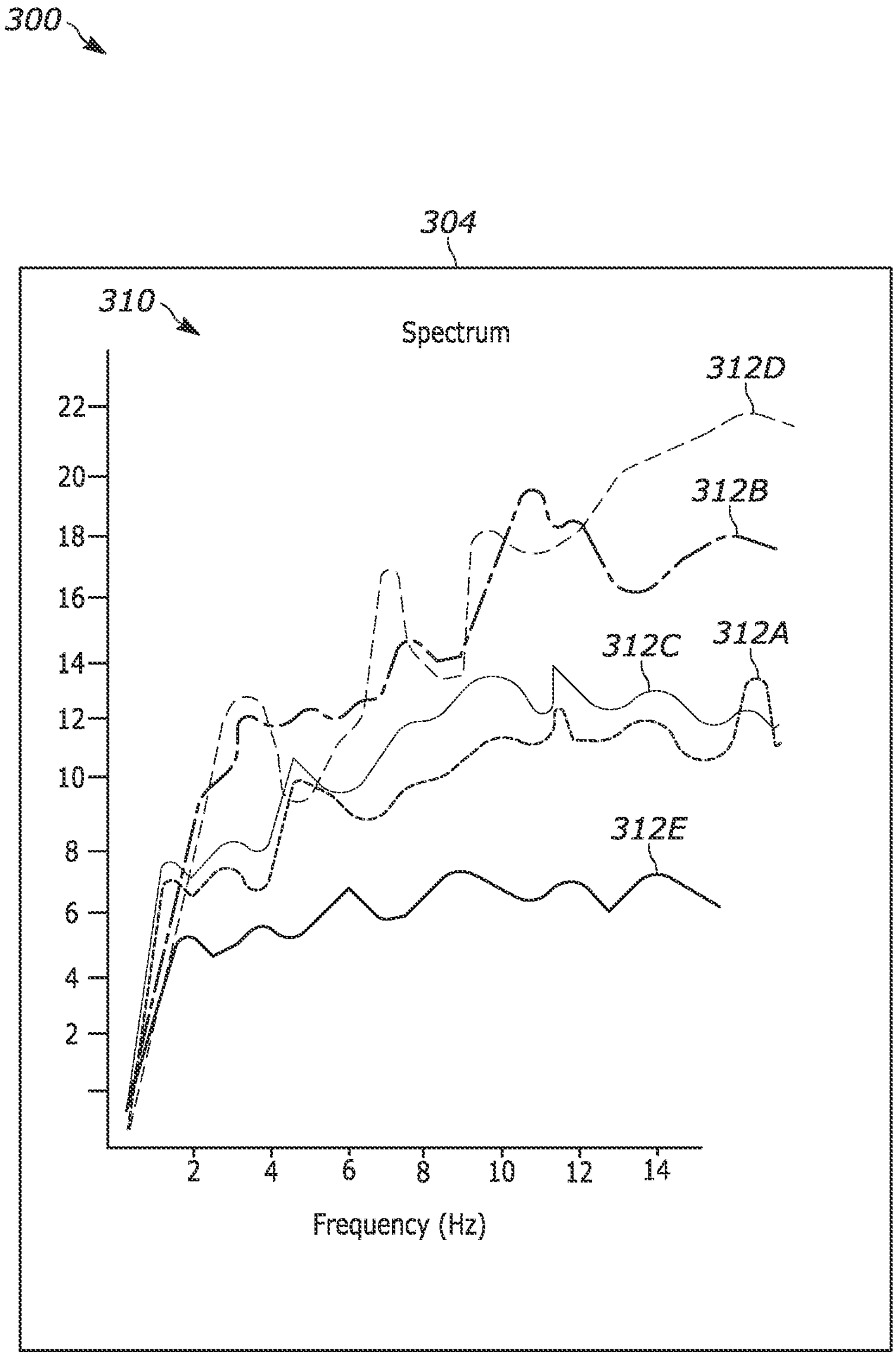
FIG. 4 illustrates a spectrum view of an output of a movement assessment device displayed on a movement assessment presentation device, in accordance with one example embodiment of the present disclosure.

At 610, a spectrum 310 is extracted from the features to identify feature variability over time. In one example embodiment, such as illustrated in FIG. 4, the spectrum 310 is displayed on the movement assessment presentation device 300. In one example embodiment the spectrum 310 is extracted for each amplitude over time 302*a*-302*e*, such that a first spectrum 312*a* corresponds to the first amplitude over time 302*a* in the first quintet 202*a*, a second spectrum 312*b* corresponds to the second amplitude over time 302*b* in the second quintet 202*b*, a third spectrum 312*c* corresponds to the third amplitude over time 302*c* in the third quintet 202*c*, a fourth spectrum 312*d* corresponds to the fourth amplitude over time 302*d* in the fourth quintet 202*d*, and a fifth spectrum 312*e* corresponds to the fifth amplitude over time 302*e* in the fifth quintet 202*e*. At 612, potential disease and/or potential disease probability is identified from the spectrum 310 based upon identified normal v. abnormal movement of the infant. At 614, the potential disease and/or potential disease probability based upon detection of normal v. abnormal movement of the infant is presented to the user on the movement assessment presentation device 300. In one example embodiment, responsive to the identification of potential disease and/or potential disease probability over a likelihood threshold (e.g., such as from identification of abnormal movement) additional tests needed to confirm a disease are presented to the user on the movement assessment presentation device 300. In another example embodiment, responsive to the identification of potential disease and/or potential disease probability over the likelihood threshold, recommended evaluations in alignment with published guidelines are presented to the user on the movement assessment presentation device 300. In another example embodiment, the spectrum 310 is presented either in real time or once completed to the user on the movement assessment presentation device 300.

Figure 7:
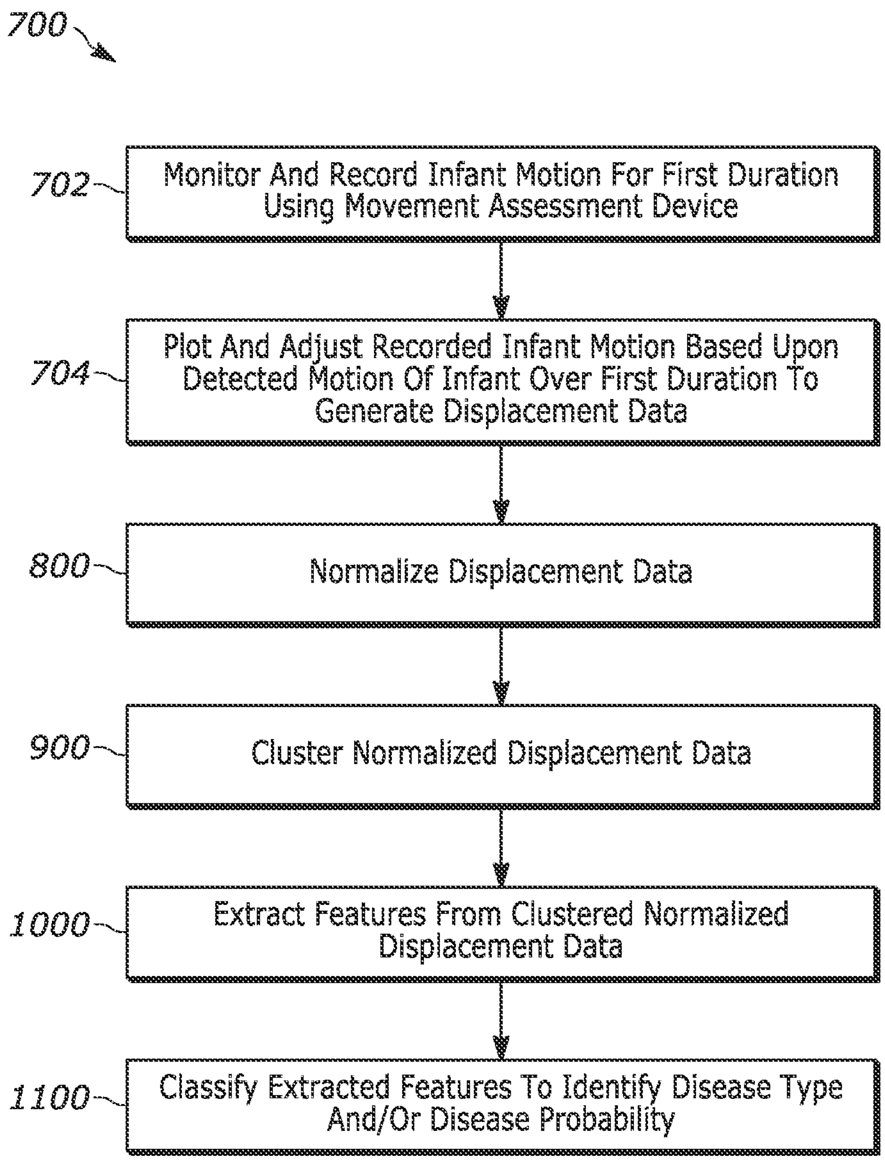
FIG. 7 illustrates a flow diagram for a method of acquiring and analyzing displacement data using a movement assessment system in accordance with one example embodiment of the present disclosure.

As shown in the example embodiment of FIG. 7, a method 700 includes steps performed by the movement assessment system 100. At 702, infant motion is monitored and recorded for a first duration using the movement assessment device 200 to generate recorded infant data. In this example embodiment, the recorded infant data comprises motion recorded for the first duration from the movement assessment device 200. In another example embodiment, responsive to the infant being placed on their back in the first orientation on the movement assessment device 200, pressure data is sampled at the first speed (e.g., 32 Hz or 32 frames per second) from the movement assessment device to generate comparable motion data. In one another example embodiment, the processing device 112 stores a record of the pressure data for the first orientation taken over the first duration.

In one example embodiment, to generate the amplitude over time 208 and/or the spectrum 310, pressure data from the movement assessment device 200 is output into a csv file with columns representing a duration or time point and rows containing pressure data for each sensor of the plurality of sensors 210. The pressure data from each duration or time point is reshaped to obtain a sensor matrix that reflects a number of sensors present in the plurality of sensors 210. The pressure data is plotted to verify that a head of the infant is located in the first orientation (e.g., corresponding to the surface labeling 1200, 1300, 1400), wherein the first orientation is wherein the head is between the first and second quintets 202*a*, 202*b* and above the third quintet 202*c*. The quintets 202 are transposed or rotated as necessary until the infant is in the first orientation. A midpoint of the pressure data as collected over time is determined to select a central 3000 timepoint matrix. In one example embodiment, the central 3000 timepoint matrix is 1500. It is contemplated that additional timepoint matrices are contemplated, both greater and lesser than 3000.

At 704, the recorded infant data is plotted and adjusted based upon detected motion of the infant over the first duration to generate displacement data. At method 800, illustrated in FIG. 8, and discussed in detail below, the displacement data is normalized to generate normalized displacement data. The normalization accounts for any differences in sensor sensitivity, thickness of clothing worn by the infant, etc. At method 900, illustrated in FIG. 9, and discussed in detail below, the normalized displacement data undergoes data clustering to generate clustered normalized displacement data. At method 1000, illustrated in FIG. 10, and discussed in detail below, the clustered normalized displacement data undergoes a feature extraction to generate extracted features. At method 1100, illustrated in FIG. 11, and discussed in detail below, the extracted features are classified to identify normal v. abnormal movement of the infant, disease type and/or disease probability.

Figure 8:
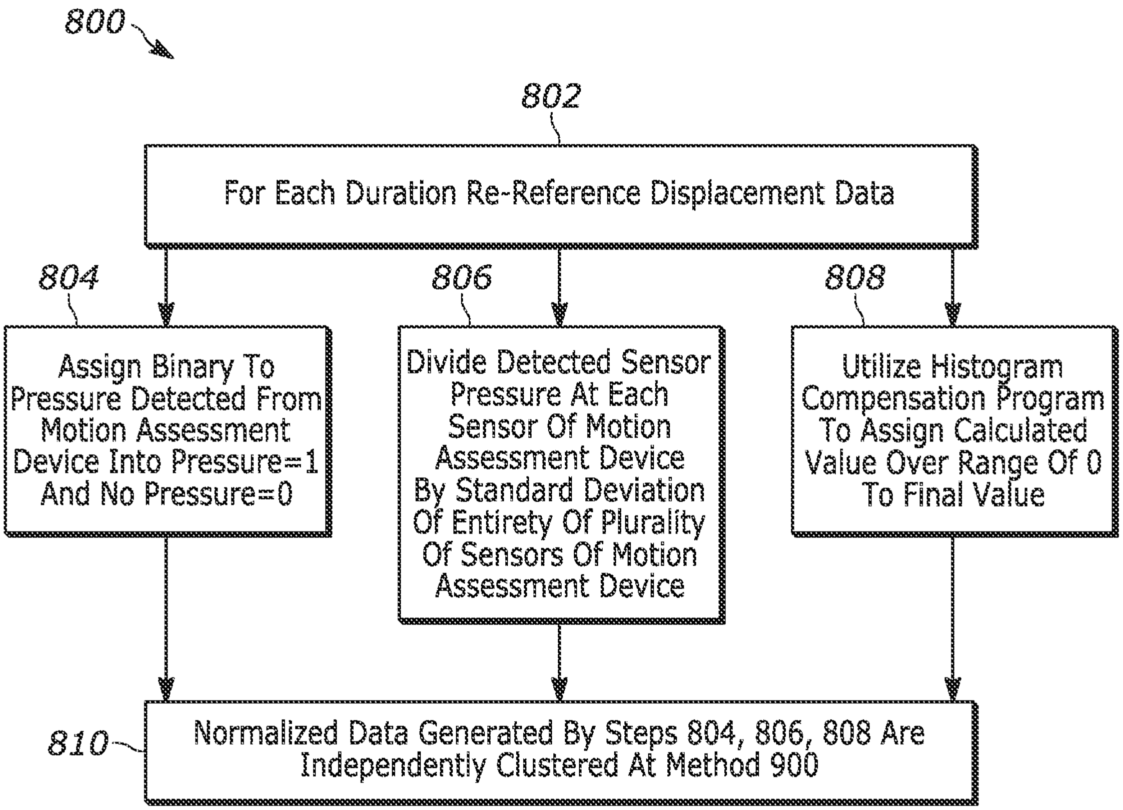
FIG. 8 illustrates a flow diagram for a method of normalizing displacement data using a movement assessment system in accordance with one example embodiment of the present disclosure.

As illustrated in FIG. 8, the method 800 of normalizing the displacement data is illustrated. At 802, each duration or time point the displacement data received from the movement assessment device 200 is referenced using steps 804, 806, and 808 in parallel. In one example embodiment, the pressure data undergoes normalization to minimize differences due to recording process and conditions (e.g., crib or mattress thickness or softness, placement of the infant, infant size, and/or weight). At 804, a binary is assigned to pressure detected from the motion assessment device 200, wherein pressure=1 and no pressure=0 (e.g., binary normalization). The binary normalization results in a binary normalized displacement data.

At 806, a detected sensor pressure for each of the plurality of sensors 210 is divided by a standard deviation of detected sensor pressure over an entirety of the plurality of sensors (e.g., standard deviation (STD) normalization). The STD normalization results in a STD normalized displacement data. At 808, a histogram compensation program is utilized to assign a calculated value over a range of 0 to a final value (e.g., histogram normalization). In one example embodiment, the range is 0-255. One example histogram compensation program is OpenCV, which is commonly used to improve grayscale images, resulting in pressure data assigned a calculated value over a range from black to white, such as assigned values 0, 255. The histogram normalization results in a histogram normalized displacement data. At 810, the binary, STD, and histogram normalized displacement data generated in method steps 804, 806, and 808 are independently clustered at method 900 illustrated in FIG. 9. In one example embodiment, the method steps 804, 806, and 808 are performed concurrently. In another example embodiment, the method steps 804, 806, and 808 are performed in series.

Figure 9:
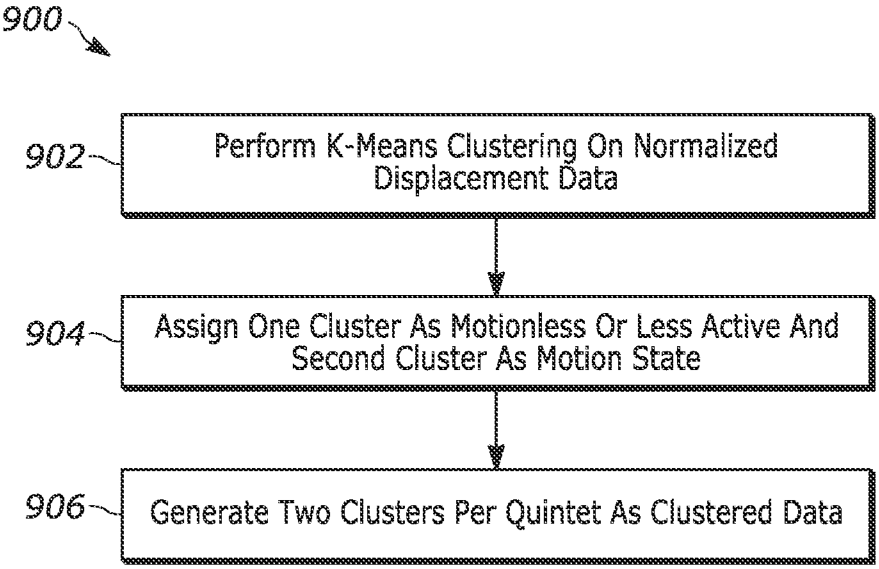
FIG. 9 illustrates a flow diagram for a method of clustering displacement data using a movement assessment system in accordance with one example embodiment of the present disclosure.

In FIG. 9, the method 900 of clustering the normalized displacement data (e.g., binary, STD, and histogram normalized displacement data) is illustrated. In one example embodiment, the clustering of method 900 is performed independently on each of the binary, STD, and histogram normalized displacement data. In another example embodiment, the clustering of method 900 is performed independently on at least one of the binary, STD, and histogram normalized displacement data.

At 902, a K-Means clustering is performed on the normalized displacement data. One example of K-Means clustering utilizes a scikits learn module. At 904, a first cluster is assigned as motionless or less active, and a second cluster is assigned as a motion state. At 906, two clusters per quintet 202 are generated as clustered data. In this example embodiment, K-Means clustering reduces aggregate durations or time points with similar variances within the normalized displacement data. The clustered data, including the independently generated binary clustered displacement data, which is the clustered data based upon the binary normalized displacement data, the STD clustered displacement data, which is the clustered data based upon the STD normalized displacement data, the histogram clustered displacement data, which is the clustered data based upon the histogram normalized displacement data is stored on the processing device 112.

Figure 10:
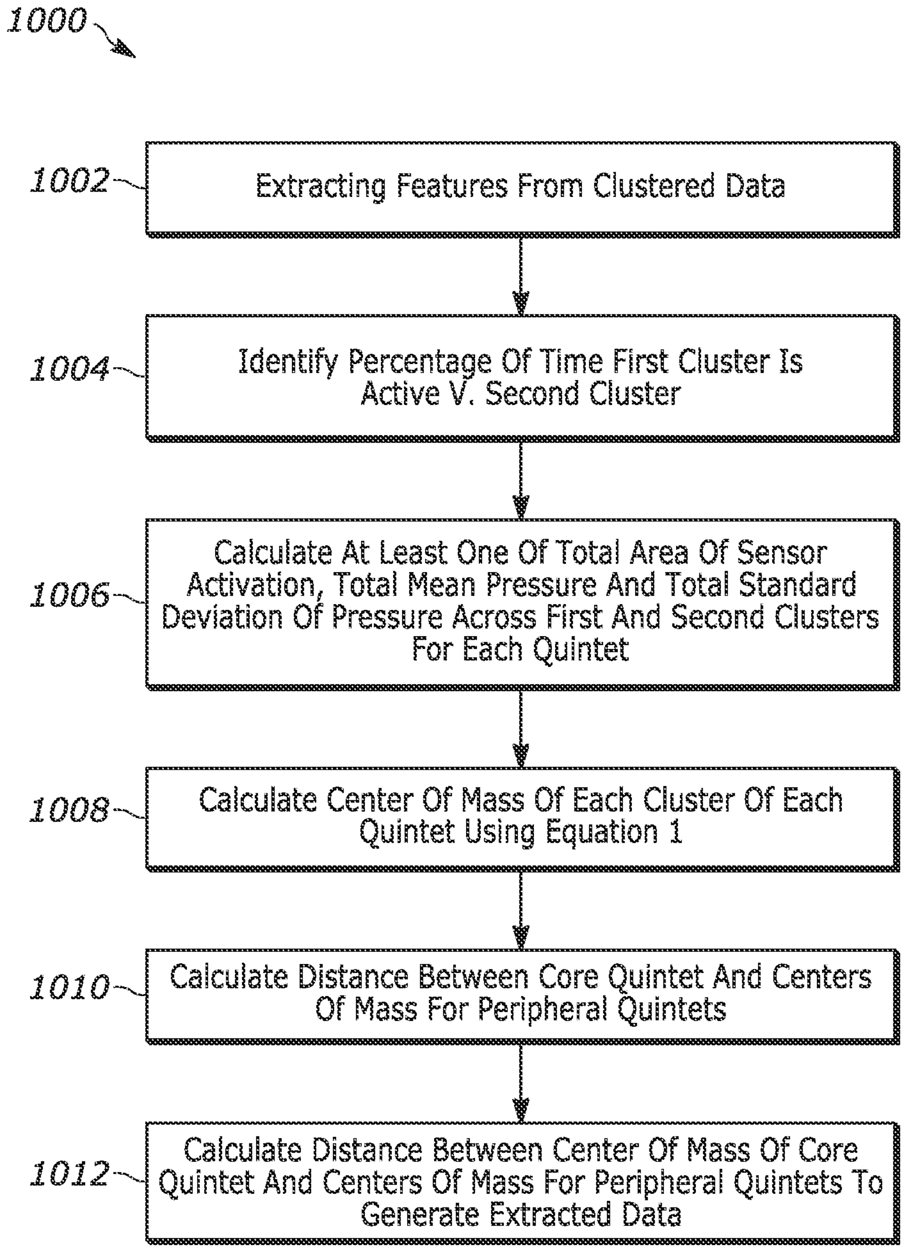
FIG. 10 illustrates a flow diagram for a method of extracting displacement data using a movement assessment system in accordance with one example embodiment of the present disclosure.

In FIG. 10, the method 1000 of extracting features from the clustered normalized displacement data is illustrated. In one example embodiment, method steps 1002-1012 are performed on the binary clustered displacement data, the STD clustered displacement data, and/or the histogram clustered displacement data, collectively referred to as the clustered data, to generate three independent extracted data sets. At 1002, features are extracted from the clustered data. At 1004, a percentage of time that a first cluster is active v. a second cluster is active is identified. In this embodiment, a first feature extracted is the percentage of time that each cluster appeared during the first duration. Stated another way, a fitting step is performed to generate comparable signal processing analyses.

At 1006, at least one of the total area of activation (equal to the number of sensors of the plurality of sensors 210 recording pressure), the total mean pressure (e.g., the total pressure over the plurality of sensors 210), and the total standard deviation (STD) of pressure across the first and second clusters are calculated. In this example embodiment, a second feature extracted is at least one of the total area of activation, the total mean pressure, and the total STD of pressure across the first and second clusters.

At 1008, the center of mass for each cluster of each quintet 202*a*-202*e* is calculated using Equation 1 below. In this example embodiment, the center of mass accounts for the difference in weight distribution of the infant across the movement assessment device 200. In one example embodiment, the center of mass includes an x and a y coordinate (e.g., that are the two barycenters of each quintet 202*a*-202*e*). The two barycenters are combined into an x, y, coordinate to comprise the center of mass. Further, each sensor of the plurality of sensors 210 includes barycentric coordinates wherein the combination of two barycentric coordinates (x, y) that represent the center of mass creates a representation of the center of the infant on the movement assessment device 200 or a center of the infant mass in a particular quintet 202*a*-202*e*, accounting for uneven distribution of the infant across the movement assessment device or across the various quintets. In one example embodiment, a third feature extracted is the centers of mass of each cluster of each quintet 202*a*-202*e*. In one example embodiment, the center of mass of each cluster is presented as a tuple (e.g., xb,yb) and given the coordinates (0,0). In this example, the center of mass is obtained by combining the barycenters 204*a*-204*e* of each quintet 202*a*-202*e* along x and y axes as shown in Equation 1, below:

$$\left\{ x = \frac{\sum_{i=1}^{32} x(i), v(i)}{\sum_{i=1}^{32} v(i)} \mid y = \frac{\sum_{i=1}^{32} y(i), v(i)}{\sum_{i=1}^{32} v(i)} \right\}$$

In Equation 1, x or y is the position of an index, and v is the pressure value from the corresponding index. In one example embodiment, indexing the tuples account for fluidity, speed and engagement of limbs of the infant during general movements.

At 1010, a distance between a core quintet (the third quintet 202*c*) and centers of mass of peripheral quintets (first, second, fourth, and fifth quintets 202*a*, 202*b*, 202*d*, 202*e*)(see FIGS. 2A, 2C) is calculated. In one example embodiment, a fourth feature extracted is the distance between the core quintet 202*c* and centers of mass of peripheral quintets 202*a*, 202*b*, 202*d*, 202*e*. In another example embodiment, the quintets 202 are defined as 3×3 sensor quintets that are defined relative to the center of mass, with the core quintet 202*c* centered on (0,0) to account for core trunk movement of the infant, and the peripheral quintets 202*a*, 202*b*, 202*d*, 202*e* are skewed outward and above/below sensors that comprise the peripheral corners of the core quintet. In this example embodiment, pressure sensed and motion identified in the peripheral quintets 202*a*, 202*b*, 202*d*, 202*e* represent the fulcra of proximal joint movements of the infant. In one example embodiment, each of the five quintets 202*a*, 202*b*, 202*c*, 202*d*, 202*e* is assigned its own calculated center mass with coordinates (x1,y1) . . . (x5,y5) as defined using Equation 1 above.

At 1012, distances 206A, 206B, 206D, 206E (see FIG. 2C) between the centers of mass 204*c* of the core quintet 202*c* and the centers of mass 204*a*, 204*b*, 204*d*, 204*e* of the peripheral quintets 202*a*, 202*b*, 202*d*, 202*e* are calculated to generate the extracted data. In one example embodiment, the distances 206*a*, 206*b*, 206*d*, 206*e* between the centers of mass 204*a*, 204*b*, 204*d*, 204*e* of the peripheral quintets 202*a*, 202*b*, 202*d*, 202*e* and the center of mass 204*c* of the core quintet 202*c* is calculated using vector products. The distances represent shifting of the fulcra compared to the core of the infant. A distance 206*c* from the center of mass 204*c* assigned as (0, 0) of core quintet 202*c* to the calculated center of mass of the core quintet 202*f* is calculated to account for breathing movements and/or large positional changes of the infant on the movement assessment device 200. In this example embodiment, a fifth feature extracted includes the calculated distances 206*a*, 206*b*, 206*d*, 206*e*.

Figure 11:
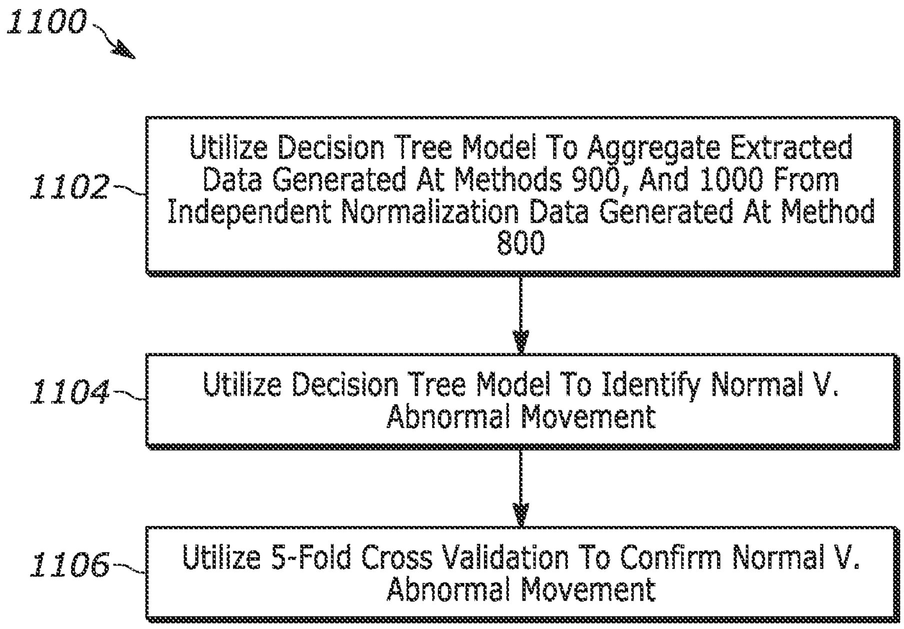
FIG. 11 illustrates a flow diagram for a method of sorting displacement data using a movement assessment system in accordance with one example embodiment of the present disclosure.

In FIG. 11, the method 1100 of aggregating the extracted features using a decision tree is illustrated. In one example embodiment, method steps 1102-1106 are utilized to aggregate the first feature extracted, the second feature extracted, the third feature extracted, the fourth feature extracted and the fifth features extracted from each of the binary clustered displacement data, the STD clustered displacement data, and/or the histogram clustered displacement data, collectively the extracted data. At 1102, a decision tree model is utilized to aggregate the extracted data generated at methods 900 and 1000 from the independent normalization data generated at method 800. In one example embodiment, the decision tree model is a supervised decision tree classifier from scikits-learn module, which predicts an outcome based on two classifications. At 1104, the decision tree is utilized to identify normal and abnormal movements. In this example embodiment, detection of normal movements is achieved as abnormal movements are differentiated from the normal movements. For example, movements that are merely poor repertoire are differentiated from abnormal movements that confer high risk for movement disorders. At 1106, a 5-fold cross validation was utilized to confirm normal v. abnormal movement. In this example embodiment, the decision tree was trained using a decision tree classifier with a 5-fold cross validation strategy. The decision tree output was a confusion matrix (true positive, true negative, false positive, and false negative). Sensitivity and specificity were then calculated.

Advantageously, the movement assessment system 100 allows for identification of abnormal movement in infants earlier than current methods, allowing for more time to implement therapy. Further, the movement assessment system 100 allows for more precise identification and referrals in the hospital, while access to specialty care is facilitated through early identification of abnormal movement/disease. Use of the movement assessment system 100 leads to improved delivery of targeted effective early interventions after the infant having the potential disease/abnormal movements is discharged. Targeted early intervention leads to known positive downstream impact on neurodevelopmental outcomes for such infants. The movement assessment system 100 does not require extensive training of users, allowing users to identify or diagnose potential disease/abnormal movements without frequent retaking of expensive and infrequent courses. Further, the surface labeling 1200, 1300, 1400 creates consistency and repeatability across users and maximize the efficacy of the movement assessment system 100. Lastly, the movement assessment system 100 helps to provide increased awareness of the importance of early detection of CP and other disorders to decrease preventable impairment and increased ability for research organizations to develop new interventions to change outcomes for infants earlier than previously possible on a systemically identified population.

In the foregoing specification, specific embodiments have been described. However, one of ordinary skill in the art appreciates that various modifications and changes can be made without departing from the scope of the disclosure as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The disclosure is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art. In one non-limiting embodiment the terms are defined to be within for example 100%, in another possible embodiment within 5%, in another possible embodiment within 1%, and in another possible embodiment within 0.5%. The term "coupled" as used herein is defined as connected or in contact either temporarily or permanently, although not necessarily directly and not necessarily mechanically. A device or structure that is "configured" in a certain way is configured in at least that way, but may also be configured in ways that are not listed.

To the extent that the materials for any of the foregoing embodiments or components thereof are not specified, it is to be appreciated that suitable materials would be known by one of ordinary skill in the art for the intended purposes.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

We claim:

1. A movement assessment system comprising:

a movement assessment device comprising a plurality of sensors, wherein the sensors of the plurality of sensors are in a substantially planar grid;

a movement assessment presentation device having a screen to display images; and a processing device in communication with the movement assessment device and the movement assessment presentation device, the processing device receiving displacement data from movement sensed by the plurality of sensors of the movement assessment device responsive to movement of a child thereon, wherein responsive to receiving the displacement data, the processing device:

identifies features from the displacement data, the features comprising at least one of motion, amplitude, and speed variation of sensed motion from the plurality of sensors;

extracts a spectrum from the features to identify feature variability over time;

identifies from the spectrum percentages of normal movement and abnormal movement;

identifies potential disease based upon the percentage of the abnormal movement over a likelihood threshold being identified; and presents the potential disease to user on the movement assessment presentation device.

2. The movement assessment system of claim 1, wherein the processing device identifies quintets comprising one or more sensors of the plurality of sensors of the movement assessment device.

3. The movement assessment system of claim 2, wherein the features are extracted from each of the quintets to generate a set of five features, and the spectrum is generated from the set of five features to generate a set of five spectrums, each reflecting sensed displacement data in one of the quintets, respectively.

4. The movement assessment system of claim 1, wherein the plurality of sensors are pressure sensors.

5. The movement assessment system of claim 1, wherein the plurality of sensors are overlaid by text or graphic representations of an orientation of a human utilizing the movement assessment system.

6. The movement assessment system of claim 1, wherein the processing device normalizes the displacement data in parallel, utilizing first, second, and third normalization structures to generate normalized displacement data, the first, second, and third normalization structures comprising different structures.

7. The movement assessment system of claim 6, wherein the first normalization structure is a binary normalization structure, the second normalization structure is a standard deviation normalization structure, and the third normalization structure is a histogram compensation normalization structure.

8. The movement assessment system of claim 7, wherein the displacement data is received and normalized as first, second, third, fourth, and fifth quintets comprising first, second, third, fourth, and fifth areas comprising one or more sensors of the plurality of sensors, the normalizing the displacement data generating normalized quintet data.

9. The movement assessment system of claim 8, wherein the processing device clusters the normalized quintet data, wherein the processing device generates two clusters per quintet as clustered data.

10. The movement assessment system of claim 6, wherein the processing device clusters the normalized displacement data using K-means clustering to generate clustered displacement data.

11. The movement assessment system of claim 9, wherein the processing device:

identifies a percentage of time the first of the two clusters per quintet is active relative to a percentage of time the second of the two clusters per quintet is active;

calculates a center of mass of each cluster of each quintet; and calculates a distance between the center of mass of a core quintet and the centers of mass of peripheral quintets to generate extracted data.

12. The movement assessment system of claim 9, wherein the processing device extracts a first feature comprising a percentage of time a first of the two clusters per quintet is active relative to a percentage of time a second of the two clusters per quintet is active;

extracts a second feature comprising a total area of activation, a total mean pressure, and a total standard deviation of pressure across the first and second clusters;

extracts a third feature comprising a centers of mass of each cluster of each quintet;

extracts a fourth feature comprising a distance between a core quintet and the centers of mass of peripheral quintets; and extracts a fifth feature comprising a distance between the center of mass of a the core quintet and the centers of mass of peripheral quintets, the features comprising extracted data.

13. The movement assessment system of claim 12, wherein the processing device utilizes a decision tree to aggregate the extracted data from the normalized displacement data.

14. The movement assessment system of claim 11, wherein the processing device utilizes a decision tree to identify the normal and the abnormal movement from the extracted data and the normalized displacement data.

15. The movement assessment system of claim 14, wherein the processing device utilizes 5-fold cross validation to confirm the identified normal and abnormal movement.

16. The movement assessment system of claim 10, wherein the processing device utilizes a decision tree to aggregate the extracted data from the normalized displacement data.

17. A non-transitory computer readable medium storing instructions executable by an associated processor to perform a method for implementing a movement assessment system, the method comprising:

receiving movement data from a movement assessment device comprising a plurality of sensors, the movement data based upon movement of an a human on the movement assessment device as detected by the plurality of sensors;

plotting recorded movement based upon the movement data taken over a first duration to generate displacement data;

normalizing the displacement data as first, second, third, fourth, and fifth quintets comprising first, second, third, fourth, and fifth areas comprising one or more sensors of the plurality of sensors, the normalizing the displacement data generating normalized quintet data;

generating two clusters per quintet as clustered data from the normalized quintet data;

generating extracted data, the generating the extracted data comprising:

identifying a first percentage of time the first of the two clusters per quintet is active relative to a second percentage of time the second of the two clusters per quintet is active;

calculating a center of mass of each cluster of each quintet based upon the first and second percentages;

calculating a distance between the center of mass of a core quintet and the centers of mass of peripheral quintets; and classifying the extracted data to identify a disease probability; and presenting to a user suggested further test or evaluations that the human should undergo based upon the disease probability.

18. The method of claim 17, wherein the normalizing the displacement data as first, second, third, fourth, and fifth quintets comprises normalizing the displacement data in parallel, utilizing first, second, and third normalization structures to generate normalized displacement data, wherein the first normalization structure is a binary normalization structure, the second normalization structure is a standard deviation normalization structure, and the third normalization structure is a histogram compensation normalization structure.

19. The method of claim 17, comprising presenting the disease probability to a user on a movement assessment presentation device.

20. A movement assessment system comprising:

a movement assessment device comprising a plurality of pressure sensors, the movement assessment device comprising surface labeling indicating where a head and feet of an infant or child should be placed;

a movement assessment presentation device having a screen to display images; and a processing device in communication with the movement assessment device and the movement assessment presentation device, the processing device receiving displacement data from the movement assessment device, wherein responsive to receiving the displacement data, the processing device:

identifies quintets comprising one or more sensors of the plurality of sensor of the movement assessment device;

extracts features from each of the quintets to generate a set of five features;

generates a set of five spectrums from the set of five features, each of the set of five spectrums reflecting sensed displacement data in one of the quintets, respectively;

identifies from the set of five spectrums percentages of normal movement and abnormal movement;

identifies potential disease based upon the percentage of the abnormal movement over a likelihood threshold being identified; and presents the potential disease to user on the movement assessment presentation device.

* * * * *